United States Patent
Hirai et al.

[11] Patent Number: 6,090,946
[45] Date of Patent: Jul. 18, 2000

[54] PROCESS FOR THE PREPARATION OF 3-(SUBSTITUTED PHENYL)-5-ALKYLIDENE-1,3-OXAZOLIDINE-2,4-DIONE DERIVATIVES

[75] Inventors: Kenji Hirai; Katsuyuki Masuda; Tomoyuki Yano; Ryuta Ohno, all of Sagamihara; Tomoko Matsukawa, Yamato; Kiyomi Imai, Okyayama; Natsuko Okano, Yamato; Tomoko Yoshii, Fujieda; Takehito Mouri, Funabashi, all of Japan

[73] Assignees: Sagami Chemical Research Center; Kaken Pharmaceutical Co., Ltd, both of Tokyo, Japan

[21] Appl. No.: 08/894,655

[22] PCT Filed: Feb. 26, 1996

[86] PCT No.: PCT/JP96/00430

§ 371 Date: Dec. 15, 1997

§ 102(e) Date: Dec. 15, 1997

[87] PCT Pub. No.: WO96/26930

PCT Pub. Date: Sep. 6, 1996

[30] Foreign Application Priority Data

Feb. 27, 1995 [JP] Japan .................................. 7-037843

[51] Int. Cl.[7] .................................................. C07D 263/44
[52] U.S. Cl. .......................................................... 548/226
[58] Field of Search .............................................. 548/226

[56] References Cited

U.S. PATENT DOCUMENTS

| 3,709,895 | 1/1973 | Kohlhaupt et al. | 548/226 |
|---|---|---|---|
| 4,220,787 | 9/1980 | Scholz | 548/226 |
| 4,294,971 | 10/1981 | Merger et al. | 548/226 |
| 4,983,751 | 1/1991 | Hirai et al. | 548/226 |
| 5,739,337 | 4/1998 | Magnus | 546/72 |

FOREIGN PATENT DOCUMENTS

| 0 004582 | 3/1979 | European Pat. Off. . |
| 0 241 559 | 10/1987 | European Pat. Off. . |
| 62-167713 | 7/1987 | Japan . |

OTHER PUBLICATIONS

Juan Riego, Antonio Costa, and Jose Manuel, "Regioselective A1PO$_4$–A1$_2$O$_3$ Promoted Ring–Opening of 2, 3–Epoxy Esters," Chemistry Letters, pp. 1565–1568, 1986 The Chemical Society of Japan.

*Primary Examiner*—Richard L. Raymond
*Attorney, Agent, or Firm*—Sughrue, Mion, Zinn, Macpeak Seas, PLLC

[57] ABSTRACT

The present invention provides an industrial process for efficiently preparing a 3-(substituted phenyl)-5-isopropylidene-1,3-oxazolidine-2,4-dione derivative having a potent herbicidal activity without using phosgene or the like. The present invention relates to a process for preparing a 3-(substituted phenyl)-5-alkylidene-1,3-oxazolidine-2,4-dione derivative represented by general formula (III), which comprises reaction of an N-(substituted phenyl)carbamate represented by general formula (I) with a 2-hydroxy-3-alkenoate represented by-general formula (II) or with a 3-alkoxy-2-hydroxyalkanoate represented by general formula (IV):

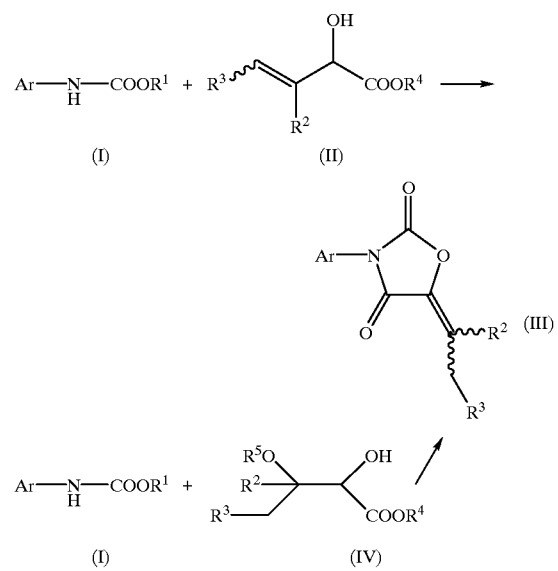

(wherein Ar is a substituted phenyl group, $R^1$ is an alkyl group having a carbon number of from 1 to 6, $R^2$ and $R^3$ are independently hydrogen atoms or alkyl groups having carbon numbers of from 1 to 12, and $R^4$ and $R^5$ are independently alkyl groups having carbon numbers of from 1 to 6).

4 Claims, No Drawings

PROCESS FOR THE PREPARATION OF 3-(SUBSTITUTED PHENYL)-5-ALKYLIDENE-1,3-OXAZOLIDINE-2,4-DIONE DERIVATIVES

TECHNICAL FIELD

The present invention relates to a process for preparing a 3-(substituted phenyl)-5-alkylidene-1,3-oxazolidine-2,4-dione derivative having a strong herbicidal effect.

BACKGROUND ART

As a process for preparing a 3-(substituted phenyl)-1,3-oxazolidine-2,4-dione derivative, the process which comprises reaction of an N-arylcarbamate with a 2-hydroxyalkanoate, if necessary, in the presence of a catalyst under heating [EP-A-0004582 (U.S. Pat. No. 4,220,787)] has been known so far. However, compounds having an alkylidene group at the 5-position can not be prepared by the process.

As a process for preparing a 3-(substituted phenyl)-5-alkylidene-1,3-oxazolidine-2,4-dione derivative, the process which comprises reaction of a (substituted phenyl) isocyanate with a 2-hydroxy-3-alkenoate in the presence of a base followed by cyclization and isomerization of the double bond [WO 87/02357 (EP-A-0241559, U.S. Pat. No. 4,818,272, U.S. Pat. No. 4983751)] is known. However, the process is not thoroughly satisfactory as an industrial process because it is necessary to use phosgene or phosgene dimer, which is extremely dangerous to handle, for preparation of the isocyanate used as a starting material in this process.

DISCLOSURE OF INVENTION

The present inventors conducted extensive research in search of a process for efficiently preparing a 3-(substituted phenyl)-5-alkylidene-1,3-oxazolidine-2,4-dione derivative having an alkylidene group at the 5-position without using dangerous phosgene or phosgene dimer, and have found that a 3-(substituted phenyl)-5-alkylidene-1,3-oxazolidine-2,4-dione derivative can be prepared in a good yield by reaction of an N-(substituted phenyl)carbamate with a 2-hydroxy-3-butenoate under heating, if necessary, in the presence of a catalyst, that likewise, a 3-(substituted phenyl)-5-alkylidene-1,3-oxazolidine-2,4-dione derivative can be prepared directly by reaction of an N-(substituted phenyl) carbamate with a 3-alkoxy-2-hydroxyalkanoate in the presence of a metallic compound as a catalyst under heating, and that the starting material, a 3-alkoxy-2-hydroxyalkanoate can be prepared by reaction of a glycidic ester with an alcohol in the presence of an acid catalyst. The present invention is accomplished on the basis of these discoveries.

The present invention provides a process for preparing a 3-(substituted phenyl)-5-alkylidene-1,3-oxazolidine-2,4-dione derivative represented by general formula (III):

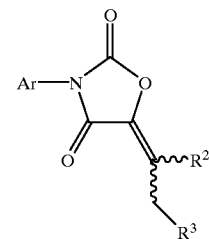

(wherein Ar is a substituted phenyl group, and $R^2$ and $R^3$ are independently hydrogen atoms or alkyl groups having carbon numbers of from 1 to 12), which comprises reaction of an N-(substituted phenyl)carbamate represented by general formula (I):

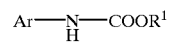

(wherein Ar is a substituted phenyl group, and $R^1$ is an alkyl group having a carbon number of from 1 to 6 or a benzyl group) with a 2-hydroxy-3-alkenoate represented by general formula (II):

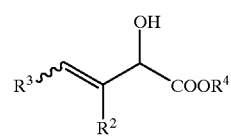

(wherein $R^2$ and $R^3$ are independently hydrogen atoms or alkyl groups having carbon numbers of from 1 to 12, and R4 is an alkyl group having a carbon number of from 1 to 6) under heating.

The present invention also provides a process for preparing a 3-(substituted phenyl)-5-alkylidene-1,3-oxazolidine-2,4-dione derivative represented by general formula (III):

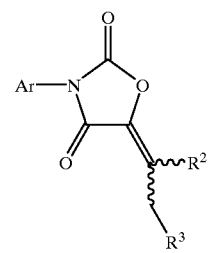

(wherein Ar is a substituted phenyl group, and $R^2$ and $R^3$ are independently hydrogen atoms or alkyl groups having carbon numbers of from 1 to 12), which comprises reaction of an N-(substituted phenyl)carbamate represented by general formula (I):

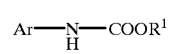

(wherein Ar is the same as defined above, and $R^1$ is an alkyl group having a carbon number of from 1 to 6 or a benzyl group) with a 3-alkoxy-2-hydroxyalkanoate represented by general formula (IV):

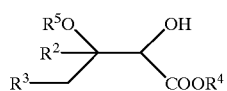

(wherein $R^2$ and $R^3$ are the same as defined above, and $R^4$ and $R^5$ are independently alkyl groups having carbon numbers of from 1 to 6) in the presence of a metallic compound as a catalyst under heating.

Further, the present invention provides a process for preparing the 3-(substituted phenyl)-5-alkylidene-1,3-oxazolidine-2,4-dione derivative represented by general formula (III), which comprises reaction of a glycidic ester represented by general formula (V):

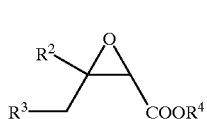

(wherein $R^2$ and $R^3$ are independently hydrogen atoms or alkyl groups having carbon numbers of from 1 to 12, and $R^4$ is an alkyl group having a carbon number of from 1 to 6) with an alcohol represented by general formula (VI):

 (VI)

(wherein $R^5$ is an alkyl group having a carbon number of from 1 to 6) in the presence of an acid catalyst to form the 3-alkoxy-2-hydroxyalkanoate represented by general formula (IV), and subsequent reaction of an N-(substituted phenyl)carbamate represented by general formula (I) with the resulting 3-alkoxy-2-hydroxyalkanoate (IV) in the presence of a metallic compound as a catalyst under heating.

Still further, the present invention provides a process for preparing the 3-alkoxy-2-hydroxyalkanoate represented by general formula (IV), which comprises reaction of the glycidic ester represented by general formula (V) with the alcohol represented by general formula (VI) in the presence of an acid catalyst.

In the process of the present invention for preparing a 3-(substituted phenyl)-5-alkylidene-1,3-oxazolidine-2,4-dione derivative (III) by using a 2-hydroxy-3-alkenoate (II) as a starting material, a base may coexist. As the base, trimethylamine, triethylamine, tripropylamine, triisopropylamine, tributylamine, triisobutylamine, tripentylamine, trihexylamine, triheptylamine, trioctylamine, tridecylamine, triphenylamine, tribenzylamine, 4-methylmorpholine, N,N-dimethylaniline, pyridine, 4-t-butylpyridine and the like may be mentioned. However, any other amines that do not have an adverse influence on the reaction may be used in the reaction. The amount of a base is preferably from 0.001 to 0.5 equivalent, more preferably from 0.01 to 0.1 equivalent relative to the substrate, although it is not particularly limited.

In this process, the reaction may also be conducted in the presence of a catalyst. As the catalyst, a metallic compound or a quaternary ammonium salt may be used, optionally in combination with the above-mentioned base. In particular, use of a metallic compound as a catalyst makes it possible to obtain the desired product in a good yield in a short time, whether it is used alone or in combination with a base. Examples of the metallic compound include fluorides, chlorides, bromides, iodides and carboxylates of iron, ruthenium, osmium, cobalt, rhodium, iridium, nickel, palladium, platinum, copper, silver, gold, zinc, cadmium, mercury, tin or lead, such as iron(II) fluoride, iron(III) fluoride, iron(II) chloride, iron(III) chloride, iron(II) bromide, iron(III) bromide, iron(II) iodide, iron(II) acetate, iron(III) acetylacetonato, ruthenium(III) chloride, ruthenium (III) bromide, ruthenium(III) iodide, osmium(III) chloride, cobalt(II) fluoride, cobalt(II) chloride, cobalt(II) bromide, cobalt(II) iodide, cobalt(II) acetate, cobalt(III) acetylacetonato, rhodium(III) chloride, rhodium(II) acetate, iridium(III) chloride, iridium(III) bromide, nickel(II) fluoride, nickel(II) chloride, nickel(II) bromide, nickel(II) iodide, nickel(II) acetate, nickel(II) acetylacetonato, palladium(II) fluoride, palladium(II) chloride, palladium(II) bromide, palladium(II) iodide, palladium(II) acetate, palladium(II) acetylacetonato, dichlorodiamineplatinum(II), chloroplatinic acid(IV), platinum(II) chloride, platinum(IV) chloride, bromoplatinic acid(IV), platinum(II) bromide, platinum(II) iodide, platinum(II) acetylacetonato, copper(II) fluoride, copper(I) chloride, copper(II) chloride, copper(I) bromide, copper(II) bromide, copper(I) iodide, copper(II) iodide, copper(I) acetate, copper(II) acetate, copper(II) acetylacetonato, silver(I) fluoride, silver(I) chloride, silver (I) bromide, silver(I) iodide, silver(I) acetate, gold(III) chloride, gold(III) bromide, gold(III) iodide, zinc(II) fluoride, zinc(II) chloride, zinc(II) bromide, zinc(II) iodide, zinc(II) acetate, zinc(II) acetylacetonato, cadmium(II) fluoride, cadmium(II) chloride, cadmium(II) bromide, cadmium(II) iodide, cadmium(II) acetate, cadmium(II) propionate, cadmium(II) acetylacetonato, mercury(I) fluoride, mercury(II) fluoride, mercury(I) chloride, mercury (II) chloride, mercury(II) bromide, mercury(II) iodide, mercury(II) acetate, tin(II) fluoride, tin(IV) fluoride, tin(II) chloride, tin(IV) chloride, tin(II) bromide, tin(IV) bromide, tin(II) iodide, tin(IV) iodide, tin(II) acetate, lead(II) fluoride, lead(II) chloride, lead(II) bromide, lead(II) iodide, lead(II) acetate, lead(II) acetylacetonato. Hydrates of these metallic compounds may also be used as a catalyst. The amount of a catalyst to be used is preferably from 0.0001 to 0.5 equivalent, more preferably from 0.001 to 0.1 equivalent relative to the substrate.

In the processes, a quaternary ammonium salt may be used as a catalyst. For example, quaternary ammonium salts including pyridinium salts which have fluoride ion, chloride ion, bromide ion, iodide ion, $BF_4^-$, $ClO_4^-$ and a sulfonate as counter anions may be mentioned. Specifically, tetramethylammonium chloride, tetramethylammonium bromide, tetramethylammonium iodide, tetramethylammonium borofluoride, tetramethylammonium perchlorate, tetramethylammonium borofluoride, tetramethylammonium p-toluenesulfonate, tetraethylammonium chloride, tetraethylammonium bromide, tetraethylammonium iodide, tetraethylammonium borofluoride, tetraethylammonium perchlorate, tetraethylammonium borofluoride, tetraethylammonium paratoluenesulfonate, tetrapropylammonium chloride, tetrapropylammonium bromide, tetrapropylammonium iodide, tetrabutylammonium chloride, tetrabutylammonium bromide, tetrabutylammonium iodide, tetrabutylammonium borofluoride, tetrabutylammonium perchlorate, tetrabutylammonium borofluoride, tetrabutylammonium paratoluenesulfonate, tetrapentylammonium chloride, tetrapentylammonium bromide, tetrapentylammonium iodide, tetrahexylammonium chloride, tetrahexylammonium bromide, tetrahexylammonium iodide, tetraheptylammonium chloride, tetraheptylammonium bromide, tetraheptylammonium iodide, tetraoctylammonium bromide, tetraoctylammonium iodide, tetraphenylammonium chloride, tetraphenylammonium bromide, tetraphenylammonium iodide, methyltrioctylammonium chloride, benzyltributylammonium chloride, benzyltriethylammonium chloride, bezyltriethylammonium bromide, ethyltripropylammonium iodide, phenyltrimethylammonium chloride, phenyltrimethylammonium bromide, phenyltriethylammonium chloride and N-alkylpyridium salts may be mentioned. Any other quaternary ammonium salts that do not have an adverse influence on the reaction may be used in the reaction. Further, pyridine salts such as pyridine hydrochloride and pyridine paratoluenesulfonate may be mentioned. The amount of a catalyst to be used is preferably from 0.0001 to 0.5 equivalent, more preferably from 0.001 to 0.1 equivalent relative to the substrate.

The process may be conducted in the absence of a solvent, but may be conducted in an appropriate organic solvent. As organic solvents, aliphatic hydrocarbon solvents such as decane, dodecane, tridecane and tetradecane, aromatic solvents such as toluene, xylene, chlorobenzene, dichlorobenzene and tetralin and mixtures thereof may be mentioned. The reaction can be conducted in any other solvents that do not have an adverse influence on the reaction.

Although the reaction temperature depends on the catalyst or the solvent used, the reaction is conducted at temperatures at which compounds do not decompose, preferably within a range of from 100 to 250° C.

In the process of the present invention for preparing a 3-(substituted phenyl)-5-alkylidene-1,3-oxazolidine-2,4-dione derivative (III) by using a 3-alkoxy-2-hydroxyalkanoate (IV) as a starting material, the reaction is conducted in the presence of a metallic compound as a catalyst. As metallic compounds, fluorides, chlorides, bromides, iodides and carboxylates of iron, ruthenium, osmium, cobalt, rhodium, iridium, nickel, palladium, platinum, copper, silver, gold, zinc, cadmium, mercury, tin, or lead may be mentioned. Iron or tin compounds are particularly preferred in terms of the reaction efficiency. For example, iron(II) fluoride, iron(III) fluoride, iron(II) chloride, iron(III) chloride, iron(II) bromide, iron(III) bromide, iron(II) iodide, iron(II) acetate, iron(III) acetylacetonato, tin(II) fluoride, tin(IV) fluoride, tin(II) chloride, tin(IV) chloride, tin(II) bromide, tin(IV) bromide, tin(II) iodide and tin(II) acetate may be mentioned. Hydrates of these metallic compounds may be used as a catalyst. The amount of a catalyst to be used is preferably from 0.0001 to 0.5 equivalent, more preferably from 0.001 to 0.1 equivalent relative to the substrate.

In the process, combined use of a metallic compound as a catalyst and a base makes it possible to obtain the desired product more efficiently in a short time. As bases, trimethylamine, triethylamine, tripropylamine, triisopropylamine, tributylamine, triisobutylamine, tripentylamine, trihexylamine, triheptylamine, trioctylamine, tridecylamine, triphenylamine, tribenzylamine, 4-methylmorpholine, N,N-dimethylaniline, pyridine, 4-t-butylpyridine and the like may be mentioned. Any other amines that do not have an adverse influence on the reaction may be used in the reaction. The amount of a base to be used is not particularly limited, but preferably from 0.001 to 0.5 equivalent, more preferably from 0.01 to 0.1 equivalent relative to the substrate.

The process may be conducted in the absence of a solvent, but may be conducted in an appropriate organic solvent. As organic solvents, aliphatic hydrocarbon solvents such as decane, dodecane and tridecane, aromatic solvents such as toluene, cumene, xylene, mesitylene, chlorobenzene, dichlorobenzene, nitrobenzene and tetralin and mixtures thereof may be mentioned. The reaction may also be conducted in any other solvents that do not have an adverse influence on the reaction. Although the reaction temperature depends on the catalyst, the base or the solvent to be used, the reaction is conducted at temperatures at which compounds do not decompose, preferably within a range of from 100 to 250° C., more preferably from 180 to 220° C.

Acid catalysts which can be used in the process of the present invention for preparing a 3-alkoxy-2-hydroxyalkanoate (IV) by using a glycidic ester (V) as a starting material are, for example, protonic acids such as sulfuric acid, p-toluenesulfonic acid, trifluoromethanesulfonic acid, phosphoric acid, perchloric acid and the like. The amount of a catalyst to be used is not particularly limited, and when a catalyst is used in an amount of from 0.0001 to 0.5 equivalent relative to the substrate, a glycidic ester, the desired 3-alkoxy-2-hydroxyalkanoate (IV) can be obtained in a good yield.

Next, preferable examples and the detailed explanations of various substituents covered by the present invention will be given below.

The alkyl groups having carbon numbers of from 1 to 6 represented as $R^1$ in general formula (I), as $R^4$ in general formula (II), as $R^4$ in general formula (IV), as $R^4$ in general formula (V) and as $R^5$ in general formula (VI) are linear or branched alkyl groups, unless otherwise noted. For example, a methyl group, an ethyl group, a propyl group, an isopropyl group, a butyl group, an isobutyl group, a sec-butyl group, a t-butyl group, a pentyl group, a neopentyl group, a 3-pentyl group, a hexyl group, a 3-hexyl group, a 3,3-dimethyl-2-butyl group and the like may be mentioned.

The alkyl groups having carbon number of from 1 to 12 represented as $R^2$ and $R^3$ in general formulae (II), (III), (IV) and (V) are linear or branched alkyl groups, unless otherwise noted. For example, a methyl group, an ethyl group, a propyl group, an isopropyl group, a butyl group, an isobutyl group, a sec-butyl group, a t-butyl group, a pentyl group, a neopentyl group, a 3-pentyl group, a hexyl group, a 3-hexyl group, a 3,3-dimethyl-2-butyl group, a heptyl group, a 2-heptyl group, a 3-heptyl group, an octyl group, a t-octyl group, a 2-octyl group, a 3-octyl group, a nonanyl group, a decyl group, a dodecyl group and the like may be mentioned.

The substituted phenyl group represented as Ar in general formulae (I) and (III) is a phenyl group substituted by at least one substituent such as a halogen atom, an alkyl group, an alkyloxy group, a cycloalkyloxy group, an alkenyloxy group, an alkynyloxy group, a lower alkyloxycarbonyloxy group, a nitro group and a cyano group. As halogen atoms, a fluorine atom, a chlorine atom, a bromine atom and an iodine atom may be mentioned. As the alkyl group, a linear or branched alkyl group having a carbon number of from 1 to 12 may be mentioned. For example, a methyl group, an ethyl group, a propyl group, an isopropyl group, a butyl group, an isobutyl group, a sec-butyl group, a pentyl group, a neopentyl group, a hexyl group, a heptyl group, an octyl group, a dodecyl group and the like may be mentioned. As the alkyloxy group, a linear or branched alkyloxy group having a carbon number of from 1 to 12 may be mentioned. For example, a methoxy group, an ethoxy group, a propyloxy group, an isopropyloxy group, a butyloxy group, an isobutyloxy group, a sec-butyloxy group, a pentyloxy group, a neopentyloxy group, a hexyloxy group, a hexyl-3-oxy group, a heptyloxy group, an octyloxy group, an octyl-2-oxy group, a dodecyloxy group and the like may be mentioned. As the cycloalkyloxy group, a cycloalkyloxy group having a carbon number of from 3 to 12 may be mentioned. For example, a cyclopropyloxy group, a cyclobutyloxy group, a cyclopentyloxy group, a cyclohexyloxy group, a cycloheptyloxy group, a cyclooctyloxy group, a cyclodecyloxy group, a cyclododecyloxy group and the like may be mentioned. As the alkenyloxy group, a linear or branched alkenyloxy group having a double bond and a carbon number of from 2 to 12 may be mentioned. For example, a vinyloxy group, an allyloxy group, a methallyloxy group, a 2-butenyloxy group, a 3-butenyloxy group, a 3-methyl-2-butenyloxy group, a 2-methyl-3-butenyloxy group, a 1-pentenyl-3-oxy group, a 2-pentenyloxy group, a 3-pentenyl-2-oxy group, a 4-pentenyloxy group, a 3-hexenyloxy group, a 3-heptenyloxy group, a 3-octenyloxy group, a 3-decanyloxy group a 3-dodecanyloxy group and the like may be mentioned. As the alkynyloxy group, a linear or branched alkynyloxy group having a triple bond and a carbon number of from 3 to 8 may be mentioned. For example, a propargyloxy group, a 1-methyl-propargyloxy group, a 1,1-dimethylpropargyloxy group, a 2-butynyloxy group, a 1-methyl-2-butynyloxy group, a 3-butynyloxy group, a 2-pentynyloxy group, a 3-pentynyloxy group, a 3-octynyloxy group and the like may be mentioned. As the lower alkyloxycarbonyloxy group, for example, a methoxycarbonyloxy group, a propyloxycarbonyloxy group, a butyloxycarbonyloxy group and the like may be mentioned.

More specific examples of the substituted phenyl group are a 2-fluorophenyl group, a 3-fluorophenyl group, a 4-fluorophenyl group, a 2-chlorophenyl group, a 3-chlorophenyl group, a 4-chlorophenyl group, a 2-bromophenyl group, a 3-bromophenyl group, a 4-bromophenyl group, a 2-iodophenyl group, a 3-iodophenyl group, a 4-iodophenyl group, a 2-methyphenyl group, a 3-methylphenyl group, a 4-methylphenyl group, a 2-ethylphenyl group, a 3-ethylphenyl group, a 4-ethylphenyl group, a 2-methoxyphenyl group, a 3-methoxyphenyl group, a 4-methylphenyl group, a 2-isopropyloxyphenyl group, a 3-isopropyloxyphenyl group, a 4-isopropyloxyphenyl group, a 2-nitrophenyl group, a 3-nitrophenyl group, a 4-nitrophenyl group, a 2-cyanophenyl group, a 3-cyanophenyl group, a 4-cyanophenyl group, a 2,3-difluorophenyl group, a 2,4-difluorophenyl group, a 2,5-diflourophenyl group, a 2,6-difluorophenyl group, a 3,4-difluorophenyl group, a 3,5-diflourophenyl group, a 2,3-dichlorophenyl group, a 2,4-dichlorophenyl group, a 2,5-dichlorophenyl group, a 2,6-dichlorophenyl group, a 3,4-diclhorophenyl group, a 3,5-diclhorophenyl group, a 2,3-dibromophenyl group, a 2,4-dibromophenyl group, a 3,4-dibromophenyl group, a 3,5-dibromophenyl group, a 4-chloro-2-fluorophenyl group, a 3-chloro-4-fluorophenyl group, a 4-bromo-2-fluorophenyl group, a 2-fluoro-5-isoproyploxyphenyl group, a 2-fluoro-5-propagyloxyphenyl group, a 2-flouro-5-methoxycarbonyloxyphenyl group, a 4-bromo-2-chlorophenyl group, a 2,3-dimethylphenyl group, a 2,4-dimethylphenyl group, a 2,5-dimethylphenyl group, a 3,4-dimethylphenyl group, a 3,5-dimethylphenyl group, a 2-fluoro-5-methylphenyl group, a 3-fluoro-4-methylphenyl group, a 3-fluoro-2-methoxyphenyl group, a 2-fluoro-5-nitrophenyl group, a 2-chloro-4-methylphenyl group, a 2-chloro-4-isopropylphenyl group, a 2-chloro-4-nitrophenyl group, a 4-chloro-2-nitrophenyl group, a 2-methyl-4-nitrophenyl group, a 4-methyl-3-nitrophenyl group, a 2-methoxy-4-nitrophenyl group, a 4-methoxy-2-nitrophenyl group, a 2,4,6-trichlorophenyl group, a 2,4,5-trichlorophenyl group, a 3,4,5-trichlorophenyl group, a 2,4,6-trifluorophenyl group, a 2,4-diclhoro-6-fluorophenyl group, a 3,5-dichloro-4-fluorophenyl group, a 3,4-dichloro-5-fluorophenyl group, a 2,4-dichloro-5-fluorophenyl group, a 6-bromo-2,4-dichlorophenyl group, a 5-bromo-2,4-dichlorophenyl group, a 6-chloro-2,4-difluorophenyl group, a 2,4-difluoro-5-methylphenyl group, a 2,4-dichloro-5-isopropyloxyphenyl group, a 5-(2-butenyloxy)-2,4-dichlorophenyl group, a 2,4-dichloro-5-propagyloxyphenyl group, a 2,4-dichloro-5-methoxycarbonyloxyphenyl group, a 2,4-diclhoro-5-nitrophenyl group, a 4-chloro-2-fluoro-5-nitrophenyl group, a 4-chloro-2-fluoro-5-isopropyloxyphenyl group, a 4-chloro-2-fluoro-5-sec-butyloxypenyl group, a 4-chloro-5-cyclopropyloxy-2-fluorophenyl group, a 4-chloro-5-cyclopentyloxy-2-fluorooxyphenyl group, a 5-allyloxy-4-chloro-2-fluorophenyl group, a 4-bromo-2-fluoro-5-propargyloxyphenyl group, a 4-chloro-2-fluoro-5-(1-methylpropargyloxy)phenyl group, a 4-chloro-2-fluoro-5-methoxyphenyl group, a 4-chloro-2-fuloro-5-methoxycarbonyloxyphenyl group and the like.

A carbamate represented by general formula (I) used as a starting material in the present invention can be synthesized, for example, by the methods disclosed in JP-A-5-17427 and EP-A-0496347 (U.S. Pat. No. 5,281,742) and can be easily produced by reacting the corresponding aniline derivative with a chloroformic ester in the presence of a base. A 2-hydroxy-3-alkenoate represented by general formula (II) used as a starting material in the present invention can be easily synthesized, for example, by the method disclosed in EP-A-0153692 (U.S. Pat. No. 4,621,150). Further, a glycidic ester represented by general formula (V) used as a staring material in the present invention can be easily synthesized, for example, by the method disclosed in Organic Reactions, Vol. V, p 413, (1960).

BEST MODE CARRYING OUT THE INVENTION

Now, the present invention will be described in more detail with reference to Examples. However, it should be understood that the present invention is by no means restricted to such specific Examples.

EXAMPLE 1

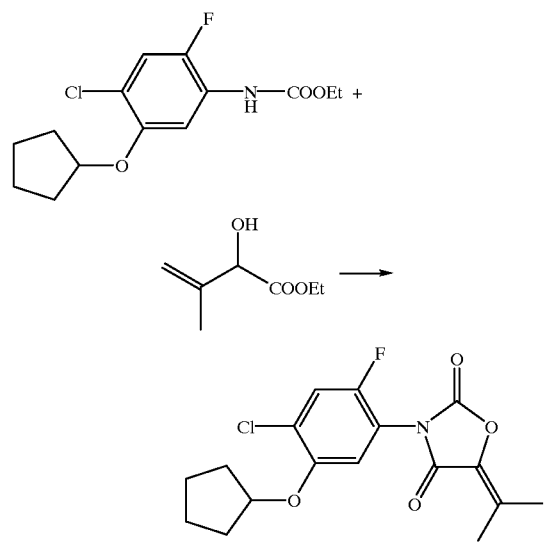

Ethyl N-(4-chloro-5-cyclopentyloxy-2-fluorophenyl) carbamate (3.01 g, 10 mmol) and ethyl 2-hydroxy-3-methyl-3-butenoate (4.32 g, 30.0 mmol) were introduced into a flask (25 cc) equipped with a distillation unit, and the reaction was conducted at 215° C. for 16.5 hours. After the reaction solution was cooled to room temperature, toluene (20 mL) was added, and then the reaction solution was washed with water (20 mL), then 1N sodium hydroxide (20 mL) and 1N hydrochloric acid (20 mL). The organic layer was dried over magnesium sulfate. After the drying agent was filtered off, the filtrate was concentrated under reduced pressure. To the resulting oily crude product, methanol (3.5 mL) acidified with hydrochloric acid was added to form a homogeneous solution. Then, 6N hydrochloric acid (0.4 mL) was further added, and the solution was left to stand at room temperature. The precipitated crystals were collected by filtration, then washed with a 10:1 mixed solvent consisting of methanol and 6N hydrochloric acid and dried to obtain 3-(4-chloro-5-cyclopentyloxy-2-fluorophenyl)-5-isopropylidene-1,3-oxazolidine-2,4-dione (1.80 g, yield 50.9%).

$^1$H-NMR(CDCl$_3$, TMS, ppm): δ 1.58–1.91 (8H,m), 2.00 (3H,s), 2.26 (3H,s), 4,73 (1H,m), 6.77 (1H,d,J$_{EF}$=6.6 Hz), 7.27 (1H,d,J$_{HF}$=8.5 Hz).

m.p.: 104.5–105° C.

IR(KBr disk, cm$^{-1}$): 1820, 1743, 1693.

EXAMPLE 2

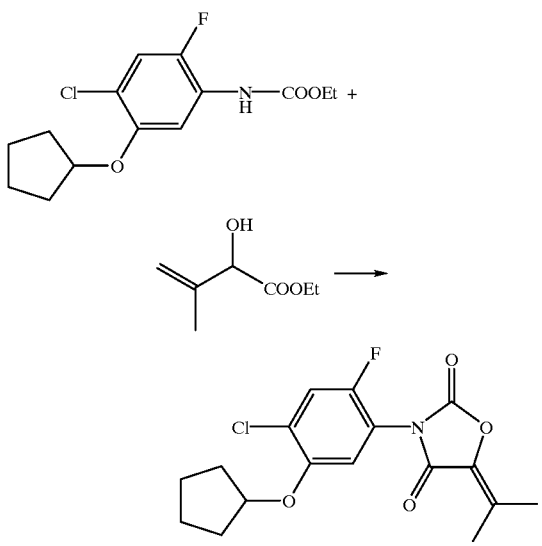

Ethyl N-(4-chloro-5-cyclopentyloxy-2-flourophenyl) carbamate (3.01 g, 10 mmol), ethyl 2-hydroxy-3-methyl-3-butenoate (4.32 g, 30 mmol) and tributylamine (92.7 mg, 0.5 mmol) were introduced into a flask (100 cc) equipped with an air condenser tube (20 cm), and the reaction was conducted at 210° C. for 15 hours under such a reduced pressure that the ethyl butenoate was refluxed below the middle of the air condenser tube. After the reaction solution was cooled to room temperature, toluene (30 mL) was added, and the reaction solution was washed with 1N sodium hydroxide (20 mL×2) and then 1N hydrochloric acid (20 mL×2). The organic layer was dried over magnesium sulfate. After the drying agent was filtered off, the filtrate was concentrated under reduce pressure. Acidic methanol (3.5 mL) was added to the resulting oily crude product to form a homogeneous solution. Then, 6N hydrochloric acid (0.4 mL) was further added, and the solution was left to stand at room temperature. The precipitated crystals were collected by filtration, washed with a mixed solvent consisting of methanol (10 mL) and 6N hydrochloric acid (2.5 mL) and dried to obtain 3-(4-chloro-5-cyclopentyloxy-2-fluorophenyl)-5-isopropylidene-1,3-oxazolidine-2,4-dione (2.53 g, yield 71.5%) as a white solid.

EXAMPLE 3

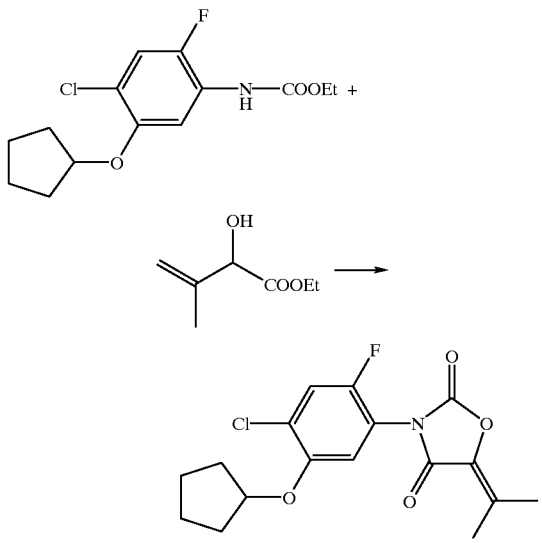

Ethyl N-(4-chloro-5-cyclopentyloxy-2-flourophenyl) carbamate (3.01 g, 10 mmol), ethyl 2-hydroxy-3-methyl-3-butenoate (4.32 g, 30 mmol), ferric chloride (162 mg, 1.0 mmol) and tributylamine (92.7 mg, 0.5 mmol) were introduced into a flask (100 cc) equipped with an air condenser tube (20 cm), and the reaction was conducted at 210° C. for 3.5 hours under such a reduced pressure that the ethyl butenoate was refluxed below the middle of the air condenser tube. After the reaction solution was cooled to room temperature, toluene (30 mL) was added, and the reaction solution was washed with 1N sodium hydroxide (20 mL×2) and then 1N hydrochloric acid (20 mL×2). The organic layer was dried over magnesium sulfate. After the drying agent was filtered off, the filtrate was concentrated under reduced pressure. Methanol (3.5 mL) acidified with hydrochloric acid was added to the resulting oily crude product to form a homogeneous solution. Then, 6N hydrochloric acid (0.4 mL) was further added, and the solution was left to stand at room temperature. The precipitated crystals were collected by filtration, washed with a 4:1 mixed solvent containing of methanol and 6N hydrochloric acid and dried to obtain 3-(4-chloro-5-cyclopentyloxy-2-fluorophenyl)-5-isopropylidene-1,3-oxazolidine-2,4-dione (2.05 g, yield 57.9%).

EXAMPLES 4 TO 7

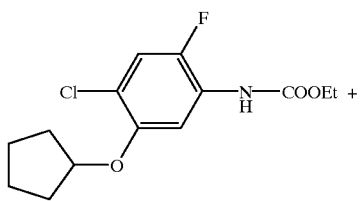

-continued

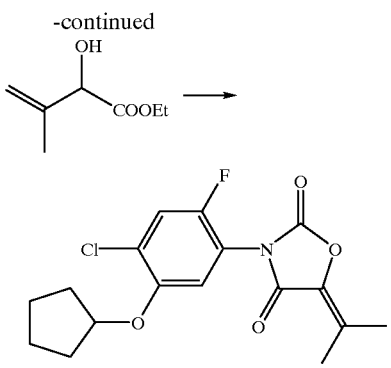

Reactions were conducted in the same manner as in Example 2 except that tin acetate, zinc chloride, lead acetate and nickel chloride were used as metallic compound catalysts. Table 1 shows the amounts of the catalysts, the reaction times and the yields of the desired product 3-(4-chloro-5-cyclopentyloxy-2-fluorophenyl)-5-isopropylidene-1,3-oxazolidine-2,4-dione.

TABLE 1

| Example | Catalyst (mg)       | Time (hr) | Yield (%) |
|---------|---------------------|-----------|-----------|
| 4       | Tin acetate (237)   | 3.5       | 74.9      |
| 5       | Zinc chloride (136) | 1.5       | 69.5      |
| 6       | Lead acetate (443)  | 4.0       | 69.0      |
| 7       | Nickel chloride (130)| 7.0      | 62.5      |

EXAMPLE 8

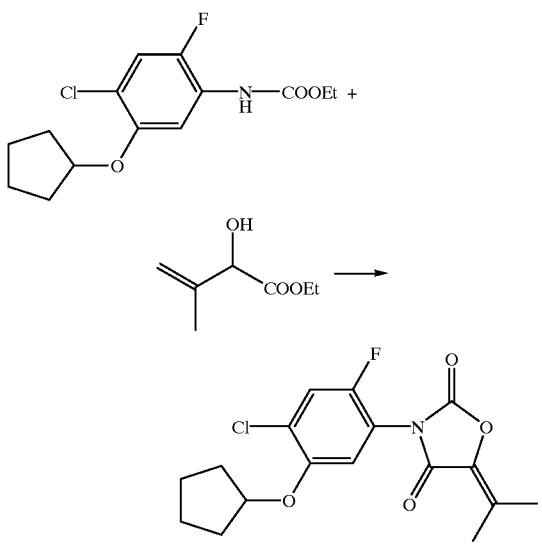

Ethyl N-(4-chloro-5-cyclopentyloxy-2-flourophenyl) carbamate (3.01 g, 10 mmol), ethyl 2-hydroxy-3-methyl-3-butenoate (2.02 g, 14 mmol) and stannous acetate (23.7 mg, 0.1 mmol) were introduced into a flask (25 cc) equipped with an air condenser tube (20 cm), and the reaction was conducted at 200° C. for 2.5 hours under such a reduced pressure that the ethyl butenoate was refluxed below the middle of the air condenser tube. After the reaction solution was cooled to room temperature, toluene (20 mL) was added, and the reaction solution was washed with water (20 mL), then 1N hydrochloric acid (20 mL), 1N sodium hydroxide (20 mL) and 1N hydrochloric acid (20 mL). The organic layer was dried over magnesium sulfate. After the drying agent was filtered off, the filtrate was concentrated under reduced pressure. Acidic methanol (3.5 mL) was added to the resulting oily crude product to form a homogeneous solution. Then, 6N hydrochloric acid (0.4 mL) was further added, and the solution was left to stand at room temperature. The precipitated crystals were collected by filtration, washed with a 20:1 mixed solvent consisting of methanol and 6N hydrochloric acid and dried to obtain 3-(4-chloro-5-cyclopentyloxy-2-fluorophenyl)-5-isopropylidene-1,3-oxazolidine-2,4-dione (1.97 g, yield 55.6%).

EXAMPLE 9

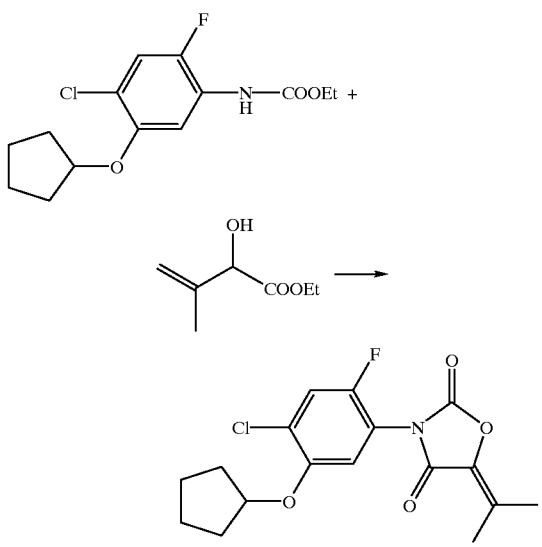

Ethyl N-(4-chloro-5-cyclopentyloxy-2-fluorophenyl) carbamate (19.6 g, 65 mmol), ethyl 2-hydroxy-3-methyl-3-butenoate (15.1 g, 105 mmol), ferric chloride (105 mg, 0.65 mmol) and tributylamine (611 mg, 3.3 mmol) were introduced into a flask (200 cc) equipped with a distillation unit, and the reaction was conducted at 200° C. for 5 hours. After the reaction solution was cooled to room temperature, toluene (100 mL) was added, and then the reaction solution was washed with 1N sodium hydroxide (100 mL×2) and 1N hydrochloric acid (100 mL×2). The organic layer was dried over magnesium sulfate. After the drying agent was filtered off, the filtrate was concentrated under reduced pressure. To the resulting oily crude product, acidic methanol (15 mL) was added to form a homogeneous solution. Then, 6N hydrochloric acid (2 mL) was further added, and the solution was left to stand at room temperature. The precipitated crystals were collected by filtration, washed with a mixed solvent consisting of methanol (20 mL) and 6N hydrochloric acid (5 mL) and dried to obtain 3-(4-chloro-5-cyclopentyloxy-2-fluorophenyl)-5-isopropylidene-1,3-oxazolidine-2,4-dione (16.7 g, yield 72.5%).

EXAMPLE 10

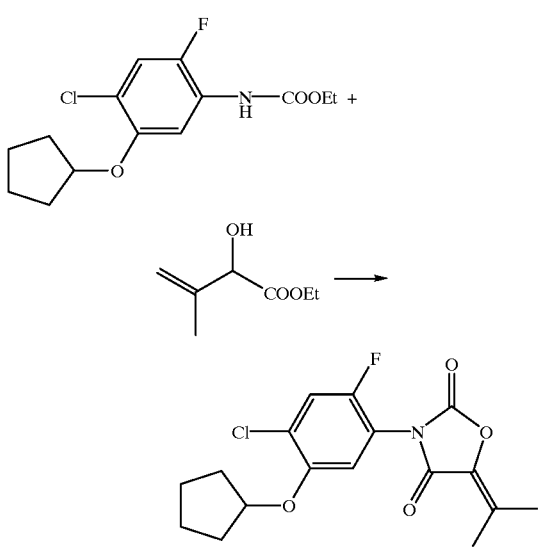

Ethyl N-(4-chloro-5-cyclopentyloxy-2-fluorophenyl) carbamate (19.6 g, 65 mmol) and ethyl 2-hydroxy-3-methyl-3-butenuate (13.4 g, 93 mmol), ferric chloride (53.5 mg, 0.33 mmol) and tributylamine (182 mg, 0.98 mmol) were introduced into a flask (200 cc) equipped with a distillation unit, and the reaction was conducted at 200° C. for 5 hours. After the reaction solution was cooled to room temperature, toluene (100 mL) was added, and then the reaction solution was washed with 1N sodium hydroxide (100 mL×2) and 1N hydrochloric acid (100 mL×2). The organic layer was dried over magnesium sulfate. After the drying agent was filtered off, the filtrate was concentrated under reduced pressure. To the resulting oily crude product, about the same volume of hexane (20 mL) was added to form a homogeneous solution, and the solution was left to stand at room temperature. The precipitated crystals were collected by filtration, washed with a small amount of hexane and dried to obtain 3-(4-chloro-5-cyclopentyloxy-2-fluorophenyl)-5-isopropylidene-1,3-oxazolidine-2,4-dione (15.7 g, yield 68.2%).

EXAMPLE 11

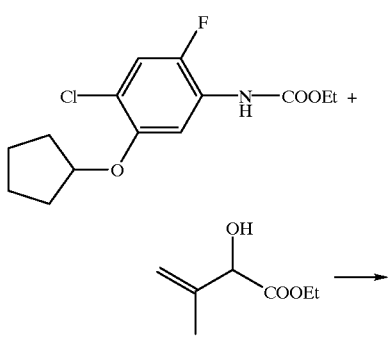

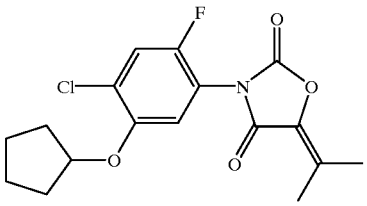

Ethyl N-(4-chloro-5-cyclopentyloxy-2-fluorophenyl) carbamate (6.02 g, 20 mmol), ferric chloride (53.5 mg, 0.33 mmol) and tributylamine (185 mg, 1.00 -mmol) were introduced into a two-necked flask (50 cc) equipped with a distillation unit and heated to 200° C. Ethyl 2-hydroxy-3-methyl-3-butenoate (4.33 g, 30 mmol) was added dropwise to the mixed solution over 30 minutes, and after the addition, the solution was stirred at 200° C. for 3.5 hours. After completion of the reaction, the reaction solution was allowed to cool to 70 to 80° C., and a mixed solution consisting of methanol (10 mL) and 6N hydrochloric acid (0.5 mL) was added thereto and mixed homogeneously. Then, the reaction solution was left to stand at room temperature. The precipitated solid was collected by filtration, washed with a mixed solution consisting of methanol (20 mL) and 6N hydrochloric acid (1 mL) and then water (20 mL) and dried completely under reduced pressure to obtain 3-(4-chloro-5-cyclopentyloxy-2-fluorophenyl)-5-isopropylidene-1,3-oxazolidine-2,4 -dione (4.77 g, yield 67.4%).

EXAMPLE 12

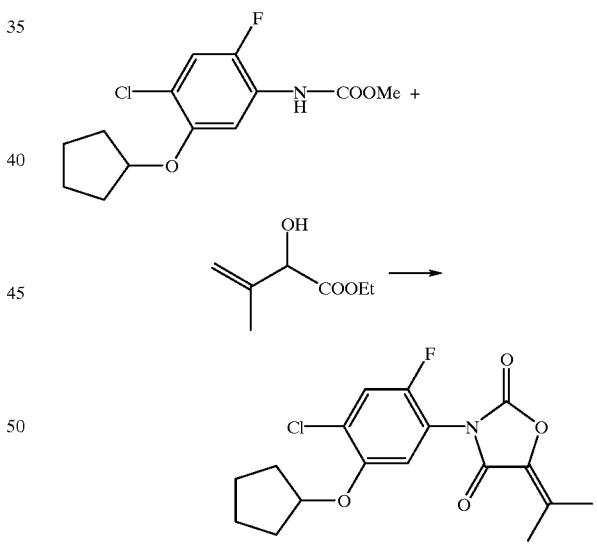

Methyl N-(4-chloro-5-cyclopentyloxy-2-fluorophenyl) carbamate (2.87 g, 10 mmol), ethyl 2-hydroxy-3-methyl-3-butenoate (4.32 g, 30 mmol), ferric chloride (162 mg, 1.0 mmol) and tributylamine (92.7 mg, 0.5 mmol) were introduced into a flask (25 cc) equipped with a distillation unit, and the reaction was conducted at 200° C. for 3 hours. After completion of the reaction, the reaction solution was allowed to cool to 70 to 80° C., and a mixed solution consisting of methanol (5 mL) and 6N hydrochloric acid (0.25 mL) was added thereto and mixed homogeneously. Then, the reaction solution was left to stand at room temperature. The precipitated solid was collected by filtration, washed with a mixed solution consisting of methanol (8 mL) and 6N hydrochloric acid (0.8 mL) and then water (10 mL) and dried completely under reduced pressure to obtain 3-(4-chloro-5-cyclopentyloxy-2-fluorophenyl)-5-isopropylidene-1,3-oxazolidine-2,4-dione (1.93 g, yield 54.5%).

EXAMPLE 13

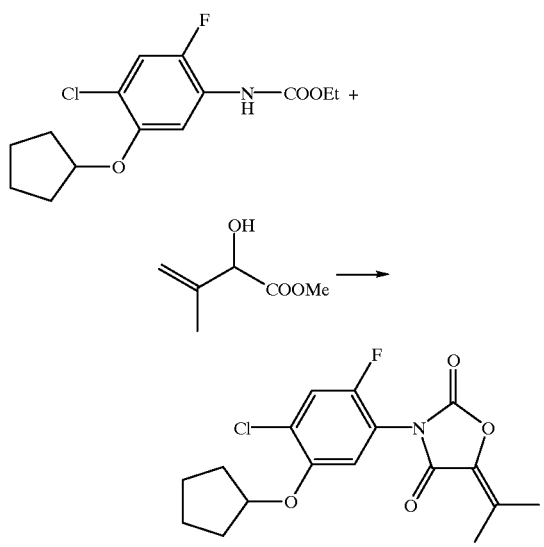

Ethyl N-(4-chloro-5-cyclopentyloxy-2-fluorophenyl) carbamate (3.01 g, 10 mmol), methyl 2-hydroxy-3-methyl-3-butenoate (3.09 g, 30 mmol), ferric chloride (162 mg, 1.0 mmol) and tributylamine (92.7 mg, 0.5 mmol) were introduced into a flask (25 cc) equipped with a distillation unit, and the reaction was conducted at 200° C. for 3 hours. After the reaction solution was cooled to room temperature, toluene (30 mL) was added, and then the reaction solution was washed with 1N sodium hydroxide (20 mL×2) and 1N hydrochloric acid (20 mL×2). The organic layer was dried over magnesium sulfate. After the drying agent was filtered off, the filtrate was concentrated under reduced pressure. To the resulting oily crude product, acidic methanol (5.0 mL) was added to form a homogeneous solution. Then, 6N hydrochloric acid (0.25 mL) was further added, and the solution was left to stand at room temperature. The precipitated crystals were collected by filtration, washed with a 20:1 mixed solvent consisting of methanol and 6N hydrochloric acid and dried to obtain 3-(4-chloro-5-cyclopentyloxy-2-fluorophenyl)-5-isopropylidene-1,3-oxazolidine-2,4-dione (2.36 g, yield 66.8%).

EXAMPLE 14

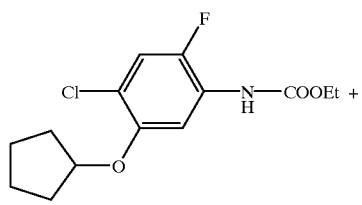

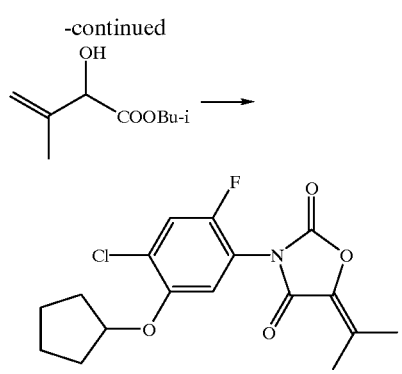

Ethyl N-(4-chloro-5-cyclopentyloxy-2-fluorophenyl) carbamate (3.01 g, 10 mmol), isobutyl 2-hydroxy-3-methyl-3-butenoate (4.22 g, 24.5 mmol) and tetrabutylammonium chloride (278 mg, 1.0 mmol) were introduced into a flask (25 cc) equipped with a distillation unit, and the reaction was conducted at 200° C. for 9 hours. After the reaction solution was cooled to room temperature, toluene (20 mL) was added, and then the reaction solution was washed with water (20 mL), then 1N sodium hydroxide (20 mL) and 1N hydrochloric acid (20 mL). The organic layer was dried over magnesium sulfate. After the drying agent was filtered off, the filtrate was concentrated under reduced pressure. To the resulting oily crude product, acidic methanol (3.5 mL) was added to form a homogeneous solution. Then, 6N hydrochloric acid (0.4 mL) was further added, and the solution was left to stand at room temperature. The precipitated crystals were collected by filtration, then washed with a mixed solvent consisting of methanol (8 mL) and 6N hydrochloric acid (0.8 mL) and then water (10 mL) and dried to obtain 3-(4-chloro-5-cyclopentyloxy-2-fluorophenyl)-5-isopropylidene-1,3-oxazolidine-2,4-dione (1.34 g, yield 37.8%).

EXAMPLE 15

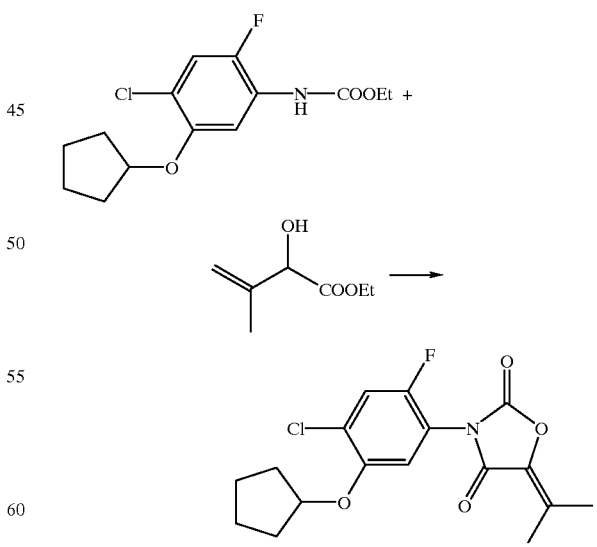

Ethyl N-(4-chloro-5-cyclopentyloxy-2-fluorophenyl) carbamate (3.01 g, 10 mmol), ethyl 2-hydroxy-3-methyl-3-butenoate (2.16 g, 15 mmol) and tetrabutylammonium chloride (278 mg, 1.0 mmol) were introduced into a flask (25 cc)

equipped with a distillation unit, and the reaction was conducted at 200° C. for 1.5 hours. After completion of the reaction, the reaction solution was allowed to cool to 70 to 80° C., and a mixed solution consisting of methanol (5 mL) and 6N hydrochloric acid (0.25 mL) was added thereto and mixed homogeneously. Then, the reaction solution was left to stand at room temperature. The precipitated solid was collected by filtration, washed with a mixed solution consisting of methanol (8 mL) and 6N hydrochloric acid (0.4 mL) and then water (10 mL) and dried completely under reduced pressure to obtain 3-(4-chloro-5-cyclopentyloxy-2-fluorophenyl)-5-isopropylidene-1,3-oxazolidine-2,4-dione (1.30 9, yield 36.7%).

EXAMPLE 16

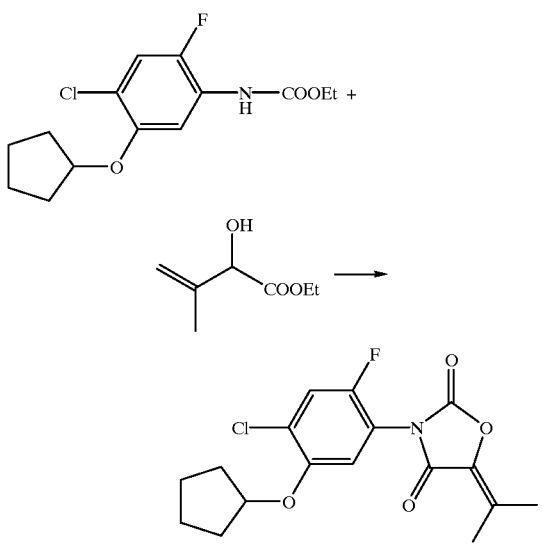

Ethyl N-(4-chloro-5-cyclopentyloxy-2-fluorophenyl) carbamate (3.01 g, 10 mmol), ethyl 2-hydroxy-3-methyl-3-butenoate (2.16 g, 15 mmol) and tetramethylammonium chloride (278 mg, 1.0 mmol) were introduced into a flask (25 cc) equipped with a distillation unit, and the reaction was conducted at 200° C. for 2 hours. After the reaction solution was cooled to room temperature, toluene (20 mL) was added, and then the reaction solution was washed with water (20 mL), then 1N sodium hydroxide (20 mL) and 1N hydrochloric acid (20 mL). The organic layer was dried over magnesium sulfate. After the drying agent was filtered off, the filtrate was concentrated under reduced pressure. To the resulting oily crude product, methanol (3.5 mL) acidified with hydrochloric acid was added to form a homogeneous solution. Then, 6N hydrochloric acid (0.4 mL) was further added, and the solution was left to stand at room temperature. The precipitated crystals were collected by filtration, then washed with a 10:1 mixed solvent consisting of methanol and 6N hydrochloric acid and dried to obtain 3-(4-chloro-5-cyclopentyloxy-2-fluorophenyl)-5-isopropylidene-1,3-oxazolidine-2,4-dione (0.323 g, yield 9.1%).

EXAMPLE 17

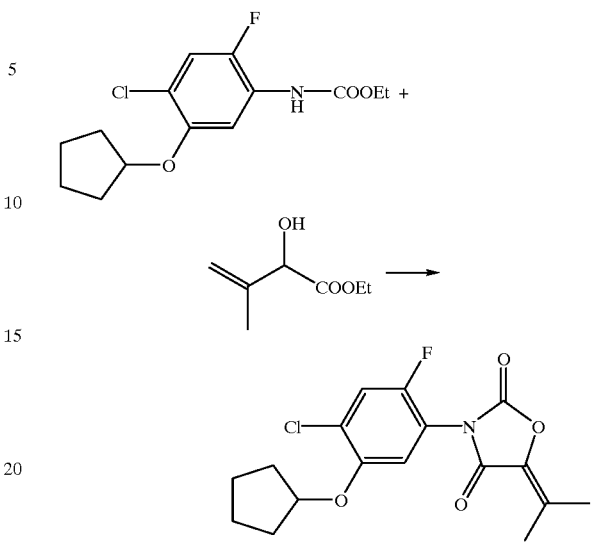

Ethyl N-(4-chloro-5-cyclopentyloxy-2-fluorophenyl) carbamate (3.01 g, 10 mmol), ethyl 2-hydroxy-3-methyl-3-butenoate (1.16 g, 11.2 mmol) and tetraethylammonium p-toluenesulfonate (151 mg, 0.50 mmol) were introduced into a flask (25 cc) equipped with a distillation unit, and the reaction was conducted at 200° C. for 3.5 hours. After the reaction solution was cooled to room temperature, toluene (20 mL) was added, and then the reaction solution was washed with water (20 mL), then 1N sodium hydroxide (20 mL) and 1N hydrochloric acid (20 mL). The organic layer was dried over magnesium sulfate. After the drying agent was filtered off, the filtrate was concentrated under reduced pressure. To the resulting oily crude product, methanol (3.5 mL) acidified with hydrochloric acid was added to form a homogeneous solution. Then, 6N hydrochloric acid (0.4 mL) was further added, and the solution was left to stand at room temperature. The precipitated crystals were collected by filtration, then washed with a 20:1 mixed solvent consisting of methanol and 6N hydrochloric acid and dried to obtain 3-(4-chloro-5-cyclopentyloxy-2-fluorophenyl)-5-isopropylidene-1,3-oxazolidine-2,4-dione (1.76 g, yield 49.7%).

EXAMPLE 18

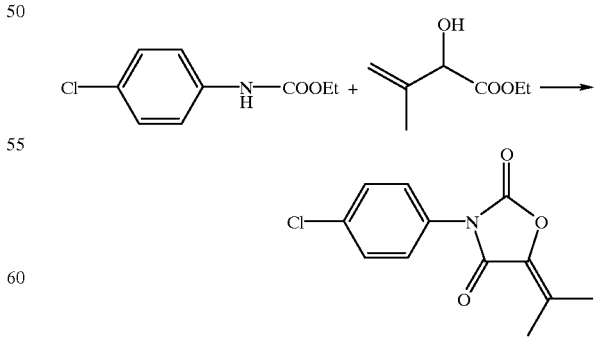

Ethyl N-(4-chlorophenyl)carbamate (2.02 g, 10.1 mmol), ethyl 2-hydroxy-3-methyl-3-butenoate (2.97 g, 22.8 mmol) and tetrabutylammonium bromide (243 mg, 1.5 mmol) were introduced into a flask (25 cc) equipped with a distillation unit, and the reaction was conducted at 200° C. for 3.5 hours. After the reaction solution was cooled to room temperature, toluene (20 mL) was added, and then the reaction solution was washed with water (20 mL), then 1N sodium hydroxide (20 mL) and 1N hydrochloric acid (20 mL). The organic layer was dried over magnesium sulfate. After the drying agent was filtered off, the filtrate was concentrated under reduced pressure. To the resulting oily crude product, a mixed solvent consisting of methanol (5 mL) and 6N hydrochloric acid (0.25 mL) was added. The precipitated solid was collected by filtration, then washed with a 10:1 mixed solvent consisting of methanol and 6N hydrochloric acid and dried to obtain 3-(4-chlorophenyl)-5-isopropylidene-1,3-oxazolidine-2,4-dione (1.03 g, yield 40.5%).

$^1$H-NMR(CDCl$_3$, TMS, ppm): δ 2.05 (3H,s), 2.00 (3H,s), 2.30 (3H,s), 7.43 (4H,s)

m.p.: 135–135.5° C.

IR(KBr disk, cm$^{-1}$): 1813, 1730, 1685.

EXAMPLE 19

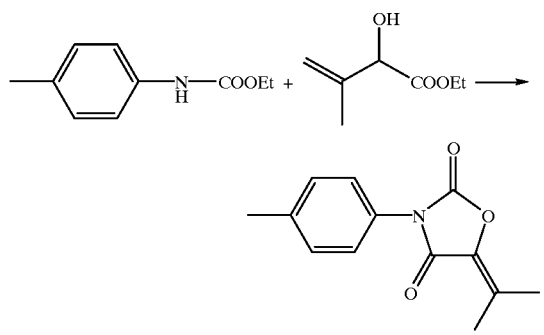

Ethyl N-(4-methylphenyl)carbamate (2.87 g, 10 mmol), ethyl 2-hydroxy-3-methyl-3-butenoate (3.90 g, 30 mmol), tetrabutylammonium chloride (139 mg, 0.5 mmol) and tributylamine (92.7 mg, 0.5 mmol) were introduced into a flask (25 cc) equipped with a distillation unit, and the reaction was conducted at 200° C. for 8 hours. After the reaction solution was cooled to room temperature, toluene (20 mL) was added, and then the reaction solution was washed with water (20 mL), then 1N sodium hydroxide (20 mL) and 1N hydrochloric acid (20 mL). The organic layer was dried over magnesium sulfate. After the drying agent was filtered off, the filtrate was concentrated under reduced pressure. To the resulting oily crude product, methanol (3.5 mL) acidified with hydrochloric acid was added to form a homogeneous solution. Then, 6N hydrochloric acid (0.4 mL) was further added, and the solution was left to stand at room temperature. The precipitated crystals were collected by filtration, then washed with a 20:1 mixed solvent consisting of methanol and 6N hydrochloric acid and dried to obtain 3-(4-methylphenyl)-5-isopropylidene-1,3-oxazolidine-2,4-dione (1.07 g, yield 46.1%).

m.p.: 135.5–136.5° C.

EXAMPLE 20

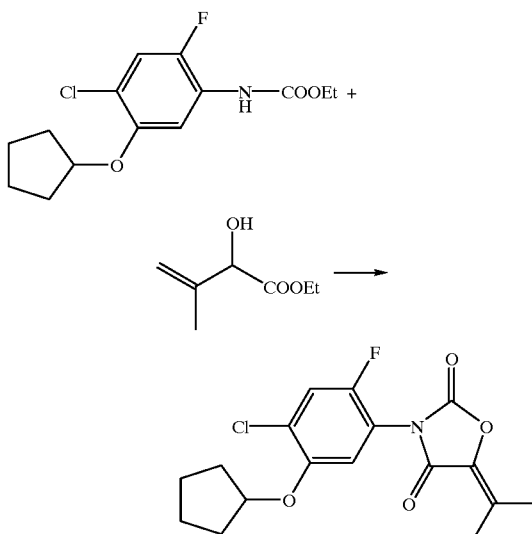

Ethyl N-(4-chloro-5-cyclopenthyloxy-2-fluorophenyl) carbamate (3.01 g, 10 mmol), ferric chloride hexahydrate (27 mg, 0.1 mmol) and triethylamine (129 mg, 1.27 mmol) were introduced into a two-necked flask (100 cc) equipped with a Dean Stark, and the resulting mixture was heated to 200° C. with stirring to form a homogeneous solution. Then, ethyl 2-hydroxy-3-methyl-3-butenoate (4.33 g, 30 mmol) was added dropwise, and after the addition, the solution was stirred for 1 hour. After completion of the reaction, the reaction mixture was treated in the same manner as in Example 2 to obtain 3-(4-chloro-5-cyclopentyloxy-2-fluorophenyl)-5-isopropylidene-1,3-oxazolidine-2,4-dione (2.70 g, yield 76.3%) as a white solid.

EXAMPLE 21

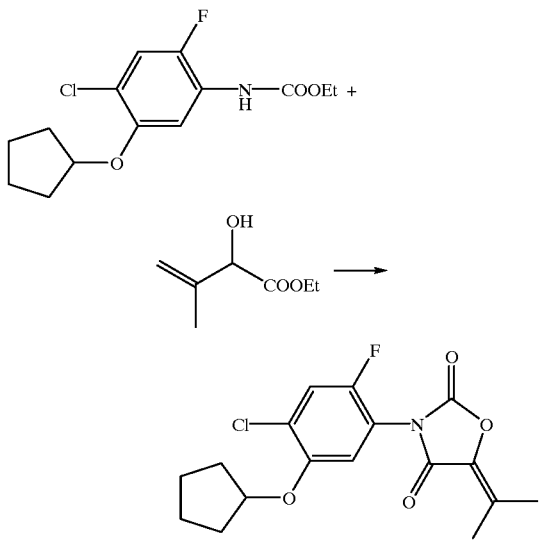

Ethyl N-(4-chloro-5-cyclopenthyloxy-2-fluorophenyl) carbamate (3.01 g, 10 mmol), ferric chloride (162 mg, 1.0 mmol) and tripentylamine (114 mg, 0.5 mmol) were introduced into a two-necked flask (100 cc) equipped with a Dean Stark, and the resulting mixture was heated to 200° C. with stirring to form a homogeneous solution. Then, ethyl 2-hydroxy-3-methyl-3-butenoate (4.33 g, 30 mmol) was added dropwise, and after the addition, the solution was stirred for 1 hour. After completion of the reaction, the reaction mixture was treated in the same manner as in Example 2 to obtain 3-(4-chloro-5-cyclpentyloxy-2-fluorophenyl)-5-isopropylidene-1,3-oxazolidine-2,4-dione (1.39 g, yield 39.3%) as a white solid.

EXAMPLE 22

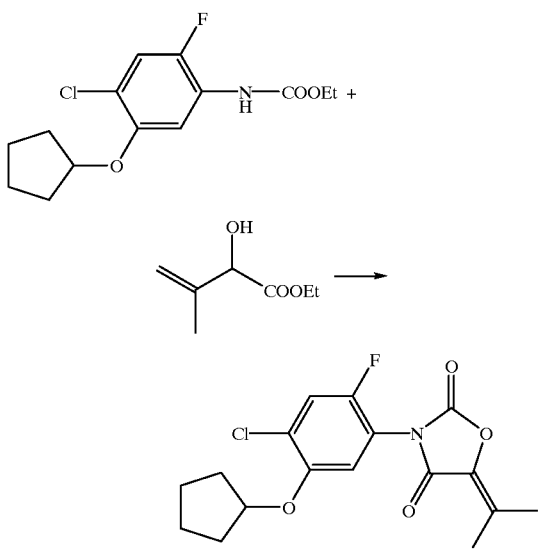

Ethyl N-(4-chloro-5-cyclopentyloxy-2-fluorphenyl) carbamate (674 g, 2.24 mmol), ferric chloride (3.7 g, 22.8 mmol) and tributylamine (21 g, 0.113 mol) were introduced into a three-necked flask (3 L) equipped with a mechanical stirrer and a Dean Stark, and the resulting mixture was heated to 200° C. with stirring to form a homogeneous solution. Then, ethyl 2-hydroxy-3-methyl-3-butenoate (484 g, 3.51 mol) was added dropwise over 5.5 hours, and after the addition, the solution was stirred for another 2.5 hours. The ethanol generated during the heating and stirring was distilled away by mean s of the Dean Stark . After completion of the reaction, the reaction mixture was allowed to cool to about 100° C., and then toluene (2.0 L) was added to form a solution. The solution was washed with 1N hydrochloric acid (1 L) and water (1 L). The organic layer was concentrated under reduced pressure, and the resulting oily crude product was crystallized in ethanol (3.85 L) acidified with sulfuric acid. The precipitated crystals were collected by filtration and washed with a small amount of acidic ethanol and then hexane to obtain 3-(4-chloro-5-cyclopentyloxy-2-fluorophenyl)-5-isopropylidene-1,3-oxazolidine-2,4-dione (590 g, yield 74.5%) as white crystals.

EXAMPLE 23

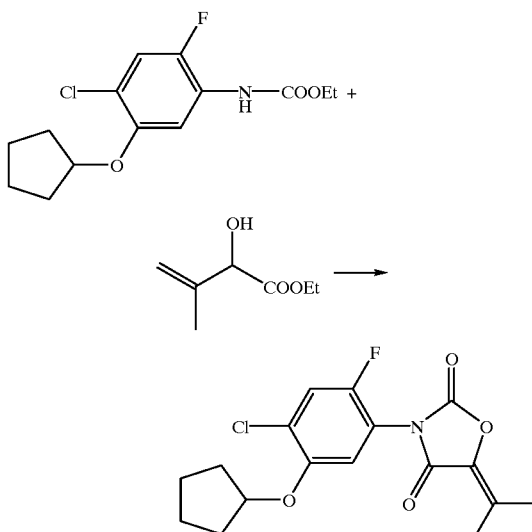

Ferric chloride hexahydrate (2.7 g, 0.01 mol), tributylamine (9.3 g, 0.05 mol) and ethyl N-(4-chloro-5-cyclopentyloxy-2-fluorophenyl)carbamate (151 g, 0.5 mol) were introduced into a three-necked flask (1 L) equipped with a mechanical stirrer and a Dean Stark, and the resulting mixture was heated to 200° C. with stirring to form a homogeneous solution. Then, ethyl 2-hydroxy-3-methyl-3-butenoate (108 g, 0.75 mol) was added dropwise over 4.8 hours, and after the addition, the solution was stirred for another 2 hours. The ethanol generated during the heating and stirring was distilled away by means of the Dean Stark. After completion of the reaction, the reaction mixture was allowed to cool to about 100° C., and then toluene (500 mL) was added to form a solution. The solution was washed with 1N hydrochloric acid (250 mL) and water (250 mL). The organic layer was concentrated under reduced pressure, and the resulting oily crude product was crystallized in ethanol (200 mL) acidified with sulfuric acid. The precipitated crystals were collected by filtration and washed with a small amount of acidic ethanol and then hexane to obtain 3-(4-chloro-5-cyclopentyloxy-2-fluorophenyl)-5-isopropylidene-1,3-oxazolidine-2,4-dione (150.5 g, yield 85.1%) as white crystals.

EXAMPLE 24

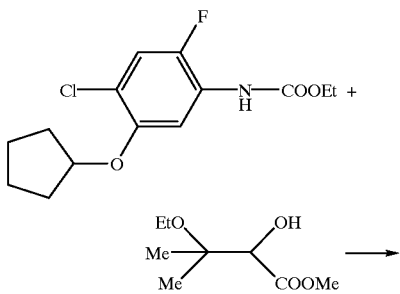

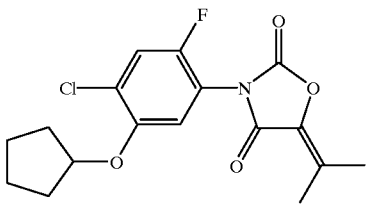

Ethyl N-(4-chloro-5-cyclopentyloxy-2-fluorophenyl) carbamate (10.0 g, 33.1 mmol), methyl 3-ethoxy-2-hydroxy-3-methylbutanoate (11.7 g, 66.4 mmol), ferric chloride (5.4 mg, 0.331 mmol) and tributylamine (0.308 g, 1.66 mmol) were introduced into a two-necked eggplant type flask (50 cc) equipped with a Dean Stark and heated at 200° C. for 4 hours with stirring. After completion of the reaction, compounds with low-boiling point were removed under reduced pressure, and the reaction mixture was cooled to room temperature. Toluene (9 mL) was added to form a homogeneous solution, and the solution was washed with 1N hydrochloric acid (25 mL×2). The organic layer was dried over anhydrous magnesium sulfate. After the drying agent was filtered off, the solvent was removed from the filtrate by distillation under reduced pressure. The resulting crude product was recrystallized from toluene/hexane to obtain 3-(4-chloro-5-cyclopentyloxy-2-fulorpyenyl)-5-isopropylidene-1,3-oxazolidine-2,4-dione as white crystals (5.27 g, yield 45.0%).

EXAMPLE 25

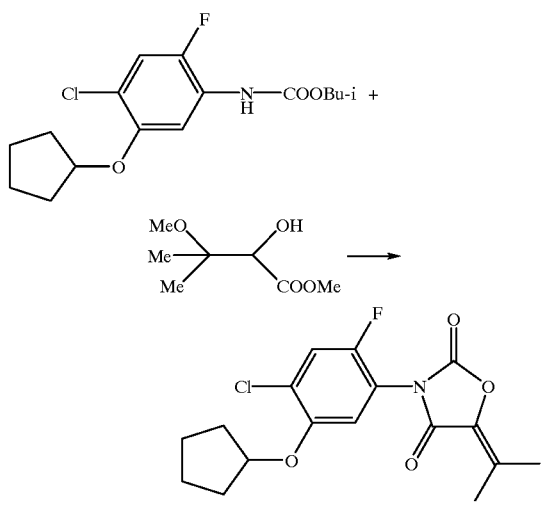

Isobutyl N-(4-chloro-5-cyclopentyloxy-2-fluorophenyl) carbamate (5.0 g, 15.2 mmol), methyl 2-hydroxy-3-methoxy-3-methylbutanoate (5.90 g, 26.4 mmol) and stannous acetate (0.50 g) were introduced into a two-necked eggplant type flask (50 cc) equipped with a Dean Stark and heated at 195–200° C. for 4 hours with stirring. After completion of the reaction, hexane (15 mL) was added, and the insolubles were filtered off. The filtrate was concentrated under reduced pressure, and the resulting oily substance was dissolved in a mixed solution consisting of benzene/hexane (1/3) and passed through a silica gel column. The developing solution was concentrated under reduced pressure, and the resulting oily substance (2.33 g) was recrystallized from methanol to obtain 3-(4-chloro-5-cyclopentyloxy-2-fluorophenyl)-5-isopropylidene-1,3-oxaszolidine-2,4-dione as white crystals (1.12 g, yield 20.9%).

EXAMPLE 26

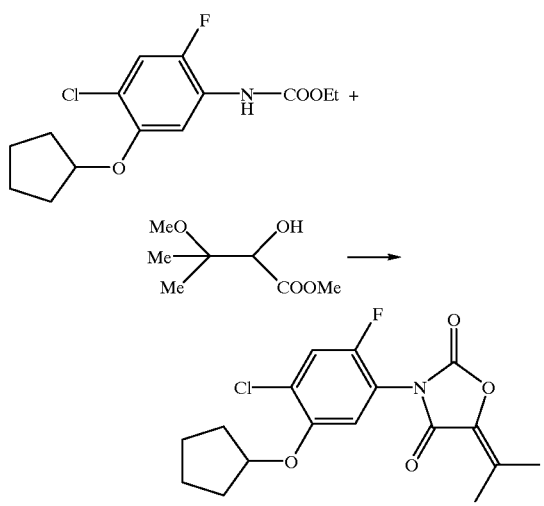

Ethyl N-(4-chloro-5-cyclopentyloxy-2-fluorophenyl) carbamate (2.00 g, 6.63 mmol), methyl 2-hydroxy-3-methoxy-3-methylbutanoate (2.69 g, 16.6 mmol) and stannous acetate (0.20 g) were introduced into a two-necked eggplant type flask (50 cc) equipped with a Dean Stark and heated at 195° C. for 3 hours with stirring. After completion of the reaction, hexane (10 mL) was added, and the insolubles were filtered off. The filtrate was concentrated under reduced pressure, and the resulting oily substance was purified through a silica gel column (benzene/hexane=1/3) to obtain 3-(4-chloro-5-cyclopentyloxy-2-fluorophenyl)-5-isopropylidene-1,3-oxazolidine-2,4-dione as white crystals (0.50 g, yield 21.3%).

EXAMPLE 27

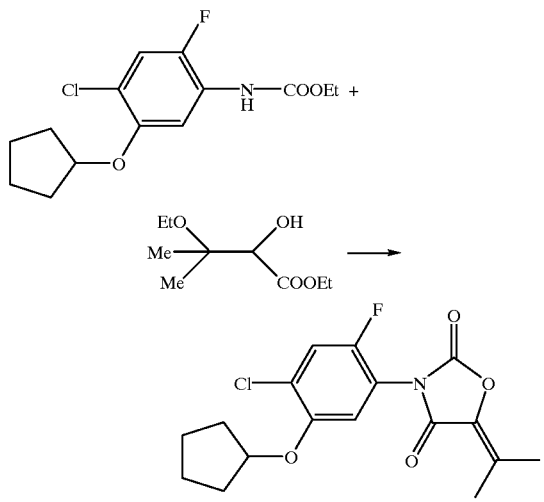

Ethyl N-(4-chloro-5-cyclopentyloxy-2 -fluorophenyl) carbamate (10.0 g, 33.1 mmol), ethyl 3-ethoxy-2-hydroxy-3-methylbutanoate (9.44 g, 49.7 mmol), ferric chloride hexahydrate (90.2 mg, 0.03 mmol) and tributylamine (309.5 mg, 1.7 mmol) were introduced into a two-necked eggplant type flask (200 cc) equipped with a Dean Stark and a Dimroth condenser and heated at 205° C. (oil bath) for 10 hours with stirring. After completion of the reaction, the reaction solution was cooled to room temperature, toluene (60 mL) was added, and the reaction solution was washed with water (100 mL). The organic layer was concentrated under reduced pressure, and ethanol (35 mL) acidified with hydrochloric acid was added to the resulting oily substance to form a homogeneous solution. The solution was left to stand at room temperature. The precipitated crystals were collected by filtration, then washed with ethanol acidified with hydrochloric acid and dried to obtain 3-(4-chloro-5-cyclopentyloxy-2-fluorophenyl)-5-isopropylidene-1,3-oxazolidine-2,4-dione as white crystals (5.40 g, yield 46.1%).

EXAMPLE 28

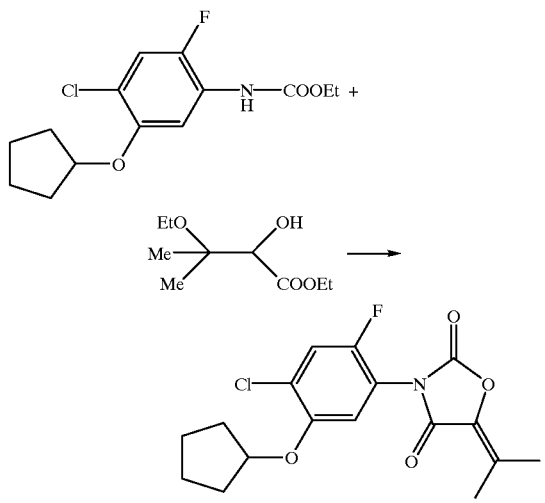

Ethyl N-(4-chloro-5-cyclopentyloxy-2-fluorophenyl) carbamate (5.0 g, 16.6 mmol), ethyl 3-ethoxy-2-hydroxy-3-methylbutanoate (8.32 g, 43.7 mmol), ferric chloride (135 mg, 0.832 mmol) and N-methylmorpholine (0.30 g, 2.97 mmol) were introduced into a two-necked eggplant type flask (50 cc) equipped with a Dean Stark and heated at 205–210° C. (oil bath) for 2.5 hours with stirring. After completion of the reaction, the reaction solution was analyzed by HPLC, and it was found that 3-(4-chloro-5-cyclopentyloxy-2-fluorophenyl)-5-isopropylidene-1,3-isopropylidene-1,3-oxazolidine-2,4-dione was formed in a yield of 77.3%.

EXAMPLE 29

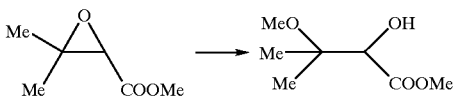

Methyl 3,3-dimethylglycidate (100 g, 0.768 mmol) and methanol (150 mL) were introduced into an eggplant type flask (500 cc) and stirred at room temperature while 70% perchloric acid (5 drops) was added gradually. The resulting reaction solution was heated at 50° C. for 2 hours with stirring. After completion of the reaction, the reaction solution was concentrated under reduced pressure, and a small amount of anhydrous sodium carbonate was added. The reaction solution was left to stand at room temperature for 15 minutes, and then the solid was removed by filtration to obtain methyl 2-hydroxy-3-methoxy-3-methylbutanoate (119.5 g, yield 96.0%) as a pale yellow liquid.

90 MHz $^1$H-NMR (CDCl$_3$,TMS,ppm): δ 1.27 (6H,s), 3.27 (1H,br,s), 3.82 (3H,s), 4.07 (1H,s).

EXAMPLE 30

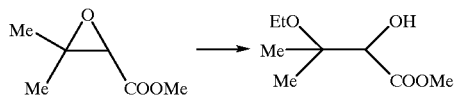

Methyl 3,3-dimethylglycidate (20.0 g, 0.154 mmol) and ethanol (30 mL) were introduced into an eggplant type flask (100 cc) and stirred at room temperature while 70% perchloric acid (5 drops) was added gradually. The resulting reaction solution was heated at 50° C. for 2 hours with stirring. After completion of the reaction, the reaction solution was concentrated under reduced pressure, and a small amount of anhydrous sodium carbonate was added. The reaction solution was left to stand at room temperature for a while, and then the solid was removed by filtration to obtain methyl 3-ethoxy-2-hydroxy-3-methylbutanoate (24.9 g, yield 91.6%) as a transparent liquid.

90 MHz $^1$H-NMR (CDCl$_3$, TMS,ppm): δ 1.13 (3H,t,J=6.5 Hz), 1.27 (6H,s), 3.07 (1H,br,s), 3.47 (2H,q,J=6.5 Hz), 3.79 (3H,s), 4.07(1H,s).

EXAMPLE 31

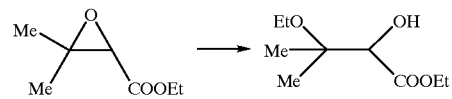

Ethyl 3,3-dimethylglycidate (73.8 g, 0.512 mol) and ethanol (250 mL) were introduced into an eggplant type flask (100 cc) and stirred at room temperature while 70% perchloric acid (5 drops) was added gradually. The resulting reaction solution was heated at 60° C. for 5 hours with stirring. After completion of the reaction, the reaction solution was concentrated under reduced pressure, and toluene (100 mL) and then sodium sulfate and a small amount of anhydrous sodium carbonate were added. The reaction solution was left to stand for a while. The solid was removed by filtration, and the solvent was removed from the filtrate under reduced pressure to obtain ethyl 3-ethoxy-2-hydroxy-3-methylbutanoate (82.2 g, yield 84.4%) as a transparent liquid.

90 MHz $^1$H-NMR (CDCl$_3$,TMS,ppm): δ 1.13 (3H,t,J=7.0 Hz), 1.27 (6H,s), 1.30 (3H,t,J=7.0 Hz), 3.17 (1H,br,s), 3.48 (2H,q,J=7.0 Hz), 4.05(1H,s), 4.28 (2H,q,J=7.0 Hz).

INDUSTRIAL APPLICABILITY

The present invention provides an industrial process for efficiently preparing a 3-(substituted phenyl)—5-alkylidene-1,3-oxazolidine-2,4-dione derivative having a strong herbicidal effect without using dangerous phosgene or phosgene dimer.

What is claimed is:

1. A process for preparing a 3-(substituted phenyl)-5-alkylidene-1,3-oxazolidine-2,4-dione derivative represented by formula (III):

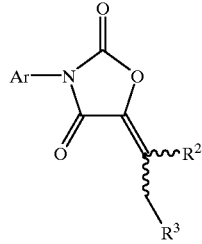
(III)

wherein Ar is a phenyl group substituted by at least one substituent selected from the group consisting of a halogen atom, an alkyl group, an alkyloxy group, a cycloalkyloxy group, an alkenyloxy group, an alkynyloxy group, a lower alkoxy carbonyl group, a nitro group and a cyano group, and $R^2$ and $R^3$ are independently hydrogen atoms or alkyl groups having carbon numbers of from 1 to 12, which comprises reaction of a carbamate represented by formula (I):

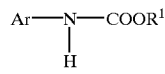
(I)

wherein Ar is a phenyl group substituted by at least one substituent selected from the group consisting of a halogen atom, an alkyl group, an alkyloxy group, a cycloalkyloxy group, an alkenyloxy group, an alkynyloxy group, a lower alkoxy carbonyl group, a nitro group and a cyano group, and $R^1$ is an alkyl group having a carbon number of from 1 to 6, with a 2-hydroxy-3-alkenoate represented by formula (II):

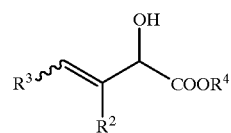
(II)

wherein $R^2$ and $R^3$ are independently hydrogen atoms or alkyl groups having carbon numbers of from 1 to 12, and $R^4$ is an alkyl group having a carbon number of from 1 to 6 at a temperature of from 100 to 250° C. in the presence of a chloride salt of iron.

2. The process according to claim 1, wherein the salt is a chloride salt.

3. The process according to claim 1, wherein the reaction is conducted in the presence of an amine.

4. The process according to claim 1, wherein the reaction is conducted in the presence of a tertiary amine.

* * * * *

UNITED STATES PATENT AND TRADEMARK OFFICE
CERTIFICATE OF CORRECTION

PATENT NO. : 6,090,946
DATED : July 18, 2000
INVENTOR(S) : Kenji Hirai et al.

It is certified that error appears in the above-identified patent and that said Letters Patent is hereby corrected as shown below:

<u>Column 28,</u>
Delete claim 2.

Signed and Sealed this

Second Day of April, 2002

Attest:

JAMES E. ROGAN
*Attesting Officer*  *Director of the United States Patent and Trademark Office*